(12) United States Patent
Park et al.

(10) Patent No.: US 10,967,164 B2
(45) Date of Patent: Apr. 6, 2021

(54) MICRO-NEEDLES AND METHOD OF MANUFACTURING THE SAME

(71) Applicant: GACHON UNIVERSITY OF INDUSTRY-ACADEMIC COOPERATION FOUNDATION, Seongnam-si (KR)

(72) Inventors: Jung Hwan Park, Seongnam-si (KR); Ji Yeon Kim, Suwon-si (KR); Jee Hyun Park, Seoul (KR); Won Jun Lee, Seongnam-si (KR)

(73) Assignee: GACHON UNIVERSITY OF INDUSTRY-ACADEMIC COOPERATION FOUNDATION, Seongnam-si (KR)

( * ) Notice: Subject to any disclaimer, the term of this patent is extended or adjusted under 35 U.S.C. 154(b) by 261 days.

(21) Appl. No.: 15/448,182

(22) Filed: Mar. 2, 2017

(65) Prior Publication Data
US 2017/0252546 A1 Sep. 7, 2017

(30) Foreign Application Priority Data

Mar. 3, 2016 (KR) .................. 10-2016-0025840
Jun. 15, 2016 (KR) .................. 10-2016-0074542

(51) Int. Cl.
*A61M 37/00* (2006.01)
*B29C 59/02* (2006.01)
(Continued)

(52) U.S. Cl.
CPC ......... *A61M 37/0015* (2013.01); *A61L 31/16* (2013.01); *B29C 39/08* (2013.01);
(Continued)

(58) Field of Classification Search
CPC .... A61K 47/36; A61K 9/0021; A61K 9/0024; A61K 38/1816; A61K 38/202;
(Continued)

(56) References Cited

U.S. PATENT DOCUMENTS

| 7,658,728 B2 | 2/2010 | Yuzhakov |
| 9,302,903 B2 | 4/2016 | Park et al. |

(Continued)

FOREIGN PATENT DOCUMENTS

| JP | 2010-233674 A | 10/2010 |
| JP | 5879927 B2 | 3/2016 |

(Continued)

OTHER PUBLICATIONS

Communication dated May 23, 2017 from the Korean Intellectual Property Office in corresponding application No. 10-2016-0025840.
(Continued)

*Primary Examiner* — Brandy S Lee
(74) *Attorney, Agent, or Firm* — Sughrue Mion, PLLC (57) ABSTRACT

Discloses is a method of manufacturing a micro-needle. The method includes a step of preparing a medicinal solution, a step of forming a plurality of tips with the medicinal solution, and a step of forming a cavity in each of the tips. In accordance with such a configuration, a micro-needle in which cavities are formed is provided, whereby it is possible to administer a fixed amount of medicine in a short time.

3 Claims, 11 Drawing Sheets

(51) Int. Cl.
- *B29C 39/08* (2006.01)
- *A61L 31/16* (2006.01)
- *B29C 41/04* (2006.01)
- B29K 105/00 (2006.01)
- A61K 9/00 (2006.01)
- A61K 47/36 (2006.01)
- B29L 31/00 (2006.01)

(52) U.S. Cl.
CPC .......... *B29C 41/045* (2013.01); *B29C 59/025* (2013.01); *A61K 9/0021* (2013.01); *A61K 9/0024* (2013.01); *A61K 47/36* (2013.01); *A61M 2037/0023* (2013.01); *A61M 2037/0038* (2013.01); *A61M 2037/0053* (2013.01); *B29K 2105/0035* (2013.01); *B29K 2105/0073* (2013.01); *B29L 2031/756* (2013.01); *B29L 2031/7544* (2013.01)

(58) Field of Classification Search
CPC ...... A61K 38/212; A61K 38/28; A61K 47/26; A61K 47/30; A61L 31/16; A61L 31/04; A61L 31/042; A61L 31/044; A61L 31/045; A61M 2037/0023; A61M 2037/0038; A61M 2037/0053; A61M 37/0015; A61M 2037/0046; B29C 39/08; B29C 41/045; B29C 59/025; B29K 2105/0035; B29K 2105/0073; B29L 2031/7544; B29L 2031/756
See application file for complete search history.

(56) References Cited

U.S. PATENT DOCUMENTS

| | | |
|---|---|---|
| 2014/0128811 A1 | 5/2014 | Ferguson et al. |
| 2015/0306363 A1* | 10/2015 | Meyer ............... A61M 37/0015 604/173 |
| 2016/0015952 A1 | 1/2016 | Omachi et al. |
| 2016/0158512 A1* | 6/2016 | Tamaru ................ B29C 39/10 604/173 |

FOREIGN PATENT DOCUMENTS

| | | |
|---|---|---|
| KR | 100781702 B1 | 12/2007 |
| KR | 1020090059971 A | 6/2009 |
| KR | 10-2011-0065361 A | 6/2011 |
| KR | 10-2011-0110665 A | 10/2011 |
| KR | 101224939 B1 | 1/2013 |
| KR | 10-1264334 B | 5/2013 |
| KR | 10-2015-0005138 A | 1/2015 |
| KR | 101513812 B1 | 4/2015 |
| KR | 10-1549086 B1 | 9/2015 |
| KR | 10-2015-0127876 A | 11/2015 |
| KR | 10-1692266 B1 | 1/2017 |
| KR | 10-1785833 B1 | 10/2017 |

OTHER PUBLICATIONS

International Search Report dated Jun. 15, 2017 issued in corresponding International Patent Application No. PCT/KR2017/001626.

Communication dated Sep. 26, 2017 from the Korean Intellectual Property Office in counterpart Patent Application No. 10-2016-0025840.

Communication dated Nov. 14, 2018, issued by the Korean Patent Office in counterpart Korean Patent Application No. 10-2016-0074542.

Communication dated Jan. 11, 2018, issued by the Korean Patent Office in counterpart Korean Patent Application No. 10-2016-0074542.

* cited by examiner

MICRO-NEEDLES AND METHOD OF MANUFACTURING THE SAME

CROSS-REFERENCE TO RELATED APPLICATION

This application claims the priority benefit of Korean Patent Application No. 10-2016-0025840, filed on Mar. 3, 2016, and Korean Patent Application No. 10-2016-0074542, filed on Jun. 15, 2016, in the Korean Intellectual Property Office, the disclosure of which is incorporated herein by reference.

BACKGROUND OF THE DISCLOSURE

Field of the Disclosure

The present disclosure relates to a micro-needle and a method of manufacturing the same, and more particularly to a micro-needle capable of shortening an administration time and allowing administration of a fixed amount of medication, and a method of manufacturing the same.

Description of the Related Art

In the case of transdermal drug delivery systems, types of drugs that can be delivered are limited depending upon the molecular weights thereof. Accordingly, various active transdermal drug delivery systems have recently been proposed. Thereamong, a method of using a micro-needle to pass through the keratin and directly administer a drug to the skin layer has attracted considerable attention. Recently, a molten micro-needle based on a water-soluble polymer has been developed. Accordingly, development of a method of administering a medicine while penetrating the skin with a tip is underway.

However, since a molten micro-needle is melted by bodily fluids after administration into the skin, ease of administration is superior, but a long time of 30 minutes or more is taken until a medicine in a tip is completely delivered. Due to such long melting period, although a molten micro-needle is removed after a predetermined administration time, an unmelted portion of the micro-needle administered into the skin is removed therewith.

Accordingly, since administration of a medicine contained in a tip depends upon complete melting of the tip, there are difficulties in delivering a fixed amount of medication to the skin. Therefore, various research into a method of improving administrability of a micro-needle has been continuously performed in recent years.

RELATED DOCUMENTS

Patent Document

Korean Patent Application Publication No. 10-2015-0127876
Japanese Patent No. 5879927
US Patent Application Publication No. 2014-0128811

SUMMARY OF THE DISCLOSURE

Therefore, the present disclosure has been made in view of the above problems, and it is an object of the present disclosure to provide a micro-needle capable of shortening an administration time and allowing administration of a fixed amount of medication, and a method of manufacturing the same.

In accordance with the present disclosure, the above and other objects can be accomplished by the provision of a micro-needle, including: a plurality of tips formed of a medicine that penetrate into and are melted in skin; and a base supporting the tips, wherein a cavity is formed in each of the tips.

The cavity may be formed between the base and each of the tips, and is formed inside, outside, or on side surfaces of each of the tips.

In accordance with another aspect of the present disclosure, there is provided a method of manufacturing a micro-needle, the method including: preparing a medicinal solution; forming a plurality of tips with the medicinal solution; and forming a cavity in each of the tips.

The forming of the cavity may include filling at least one groove formed in a mold with the medicinal solution; centrifuging the medicinal solution filled in the groove; and drying the medicinal solution and then removing the mold from the dried medicinal solution.

The forming of the cavity may include applying the medicinal solution to a supporter; vertically drawing the medicinal solution from the supporter until the cavity is formed; and drying the medicinal solution.

The medicinal solution may be prepared by mixing a biocompatible material with distilled water.

The biocompatible material may include any one or more selected from the group consisting of hyaluronic acid, alginic acid, pectin, carrageenan, chondroitin(sulfate), dextran (sulfate), chitosan, polylysine, collagen, gelatin, carboxymethyl chitin, fibrin, agarose, pullulan polylactide, polyglycolide (PGA), a polylactide-glycolide copolymer (PLGA), hyaluronic acid, alginic acid, carrageenan, chondroitin(sulfate), dextran(sulfate), chitosan, polylysine, collagen, gelatin, carboxymethyl chitin, fibrin, agarose, pullulan polyanhydride, polyorthoester, polyetherester, polycaprolactone, polyesteramide, poly(butyric acid), poly (valeric acid), polyurethane, polyacrylate, an ethylene-vinyl acetate polymer, acryl-substituted cellulose acetate, non-degradable polyurethane, polystyrene, polyvinyl chloride, polyvinyl fluoride, poly(vinylimidazole), chlorosulfonate polyolefin, polyethylene oxide, polyvinylpyrrolidone (PVP), polyethylene glycol (PEG), polymethacrylate, hydroxypropyl methylcellulose (HPMC), ethyl cellulose (EC), hydroxypropyl cellulose(HPC), carboxymethyl cellulose, cyclodextrin, and a copolymer of monomers and cellulose forming such a polymer.

The medicinal solution may be prepared by mixing a biocompatible material with an additive for increasing mechanical strength.

The additive may be formed of one or more selected from the group consisting of trehalose, glucose, maltose, lactose, lactulose, fructose, turanose, melitose, melezitose, dextran, sorbitol, xylitol, palatinit, mannitol, poly((lactide), poly(glycolide), poly((lactide-co-glycolide), polyanhydride, polyorthoester, polyetherester, polycaprolactone, polyesteramide, poly(butyric acid), poly(valeric acid), polyurethane, polyacrylate, an ethylene-vinyl acetate polymer, acryl-substituted cellulose acetate, non-degradable polyurethane, polystyrene, polyvinyl chloride, polyvinyl fluoride, poly(vinylimidazole), chlorosulphonate polyolefin, polyethylene oxide, polyvinylpyrrolidone (PVP), polyethylene glycol (PEG), polymethacrylate, hydroxypropyl methylcellulose (HPMC), ethyl cellulose (EC), hydroxypropyl cellulose (HPC), carboxymethyl cellulose, and cyclodextrin and a copolymer of monomers forming such a polymer.

The medicinal solution may be prepared by mixing a biocompatible material with an effective ingredient.

The effective ingredient may include at least one of a protein/peptide medicine, a hormone, a hormone analogue, an enzyme, an enzyme inhibitor, a signal transduction protein or a portion thereof, an antibody or a portion thereof, a single-chain antibody, a binding protein or a binding domain thereof, an antigen, an adherent protein, a structural protein, a regulatory protein, a toxin protein, a cytokine, a transcription regulator, a blood coagulation factor, and a vaccine.

The protein/peptide medicine may include at least one of insulin, insulin-like growth factor 1 (IGF-1), growth hormone, erythropoietin, granulocyte-colony stimulating factors (G-CSFs), granulocyte/macrophage-colony stimulating factors (GM-CSFs), interferon alpha, interferon beta, interferon gamma, interleukin-1 alpha and beta, interleukin-3, interleukin-4, interleukin-6, interleukin-2, epidermal growth factors (EGFs), calcitonin, adrenocorticotropic hormone (ACTH), tumor necrosis factor (TNF), atobisban, buserelin, cetrorelix, deslorelin, desmopressin, dynorphin A (1-13), elcatonin, eleidosin, eptifibatide, growth hormone releasing hormone-II (GHRH-II), gonadorelin, goserelin, histrelin, leuprorelin, lypressin, octreotide, oxytocin, pitressin, secretin, sincalide, terlipressin, thymopentin, thymosine, triptorelin, bivalirudin, carbetocin, cyclosporine, exedine, lanreotide), luteinizing hormone-releasing hormone (LHRH), nafarelin, parathyroid hormone, pramlintide, enfuvirtide (T-20), thymalfasin, and ziconotide.

The medicinal solution may include a solvent for dissolving the biocompatible material and is a mixed solution.

The solvent may include an inorganic or organic solvent such as distilled water (DI water), methanol, ethanol, chloroform dibutyl phthalate, dimethyl phthalate, ethyl lactate, glycerin, isopropyl alcohol, lactic acid, or propylene glycol.

In accordance with another aspect of the present disclosure, there is provided a micro-needle, including: a plurality of tips formed of a medicine that penetrate into and are melted in skin; and a base supporting the tips, wherein at least one cavity, in which the medicinal solution is not present, is formed in each of the tips, wherein a size of the at least one cavity is controlled by adjusting an amount, evaporation rate, and evaporation temperature of the medicinal solution, an interior shape of a mold for manufacturing the tips, a viscosity of the medicinal solution, a concentration of the medicinal solution, a used solvent type, and a thickness of the medicinal solution applied to tip grooves.

The at least one cavity may be formed in at least one portion of an interior, exterior, and middle part of each of the tips, and a base-biased part between each of the tips and the base.

The medicinal solution may be prepared by mixing a biocompatible material with distilled water.

In accordance with yet another aspect of the present disclosure, there is provided a method of manufacturing a micro-needle, the method including: preparing a medicinal solution; and forming a plurality of tips, in each of which at least one cavity is formed, with the medicinal solution, wherein the at least one cavity is formed in at least one portion of an interior, exterior, and middle part of each of the tips, and a base-biased part between each of the tips and the base.

The forming of the plurality of tips may include filling at least one groove included in a mold with the medicinal solution; drying the medicinal solution filled in the at least one groove such that the at least one cavity is formed; and removing the mold from the dried the medicinal solution.

The drying may be any one of natural drying, vacuum drying, and drying under pressure.

In the drying, the medicinal solution filled in the at least one groove may be cooled under a reduced pressure or a normal pressure and thus solidified.

In the forming of the plurality of tips, a size of the at least one cavity may be controlled by adjusting an amount, evaporation rate, and evaporation temperature of the medicinal solution, an interior shape of a mold for manufacturing the tips, a viscosity of the medicinal solution, a concentration of the medicinal solution, a used solvent type, and a thickness of the medicinal solution applied to tip grooves.

BRIEF DESCRIPTION OF THE DRAWINGS

The above and other objects, features and other advantages of the present disclosure will be more clearly understood from the following detailed description taken in conjunction with the accompanying drawings, in which.

DETAILED DESCRIPTION OF THE DISCLOSURE

Hereinafter, preferred embodiments of the present disclosure are described with reference to the accompanying drawings.

Figure 1:
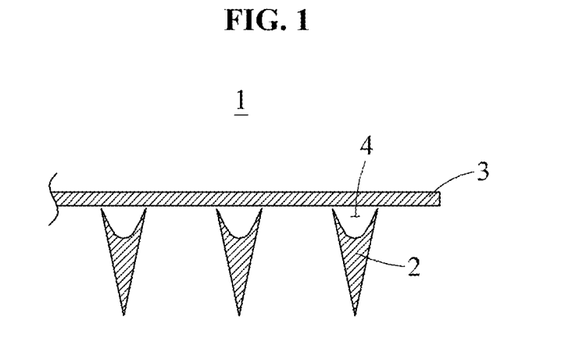
FIG. 1 illustrates a schematic sectional view of a micro-needle according to a preferred embodiment of the present disclosure.
Figure 2:
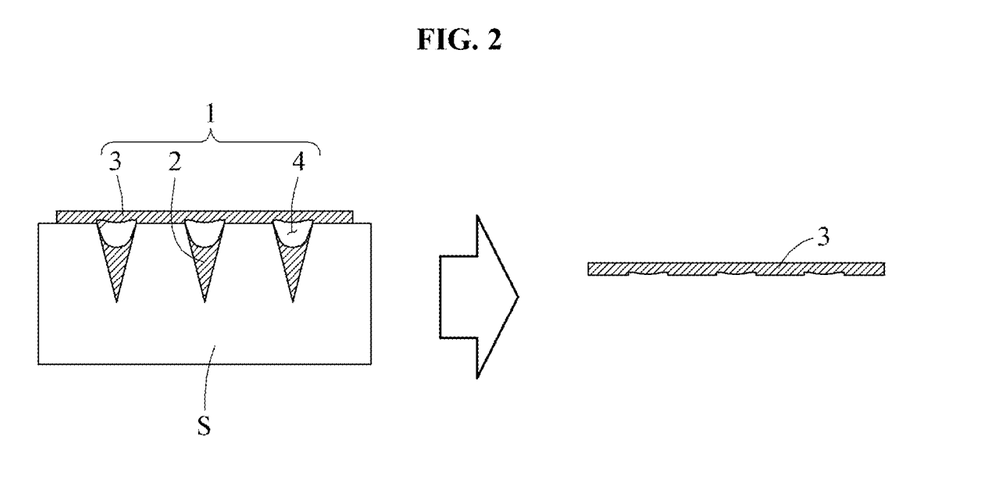
FIG. 2 illustrates a schematic sectional view of the micro-needle, illustrated in FIG. 1, penetrating the skin.

Referring to FIGS. 1 and 2, a micro-needle 1 according to a preferred embodiment of the present disclosure includes tips 2 and a base 3.

A plurality of tips 2 penetrate the skin S and are formed of a molten medicine. End portions of the tips 2 have a sharp shape to facilitate penetration of the skin. In this embodiment, the tips 2 are shown as having a polygonal pyramid shape such as a cone or a quadrangular pyramid, but the present disclosure is not limited thereto. The number of the tips 2 is also not limited to those illustrated in the drawings. Meanwhile, an empty space, i.e., a cavity, is provided in each of the tips 2. The configuration of the tips 2 including such a cavity is described in detail below.

The base 3 supports the tips 2. That is, the base 3, which simultaneously supports the tips 2, is a body of the micro-needle 1. Here, a surface, on which the tips 2 are provided, of the base 3 may be attached to the skin S, as illustrated in FIG. 2.

For reference, in accordance with the present disclosure, an empty space, i.e., a cavity 4, is formed between each of the tips 2 and the base 3. According to such a configuration, since the tips 2, which have been injected into the skin, rapidly penetrate the skin, the tips 2 do not remain on the base 3 although the base 3 is separated from the skin S, as illustrated in FIG. 2.

This embodiment illustrates the cavity 4 as formed in the interior of each of the tips 2, but the present disclosure is not limited thereto. That is, a formation site of the cavity 4 may be varied. For example, the cavity 4 may be formed outside or on side surfaces of the tips 2.

Figure 3:
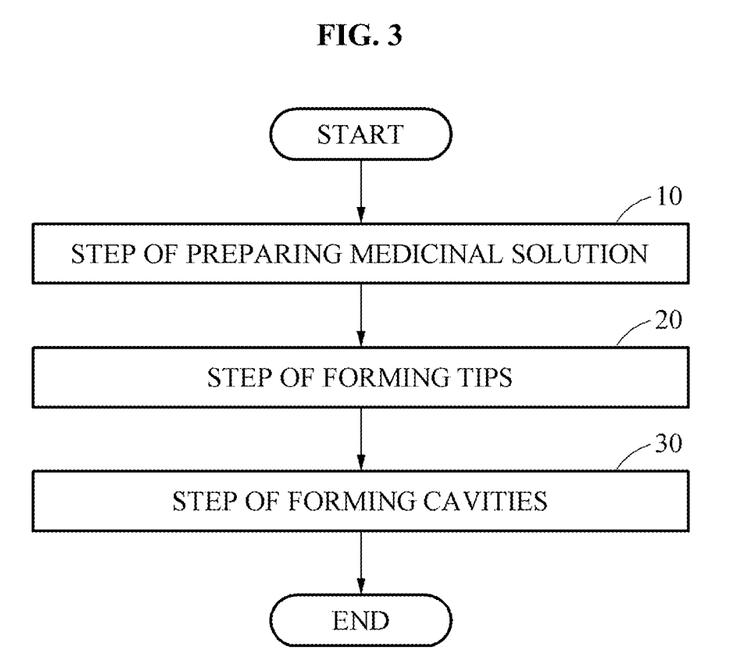
FIG. 3 is a flowchart schematically showing a method of manufacturing a micro-needle according to the present disclosure.

A method of manufacturing the micro-needle 1 according to the present disclosure is illustrated in FIG. 3.

Figure 4:
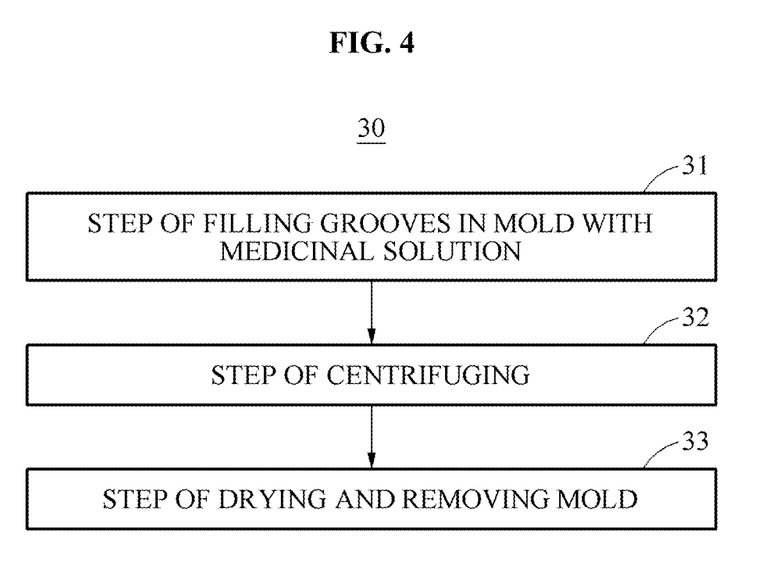
FIG. 4 is a flowchart schematically showing sub-steps of a step of forming cavities illustrated in FIG. 3.
Figure 5:
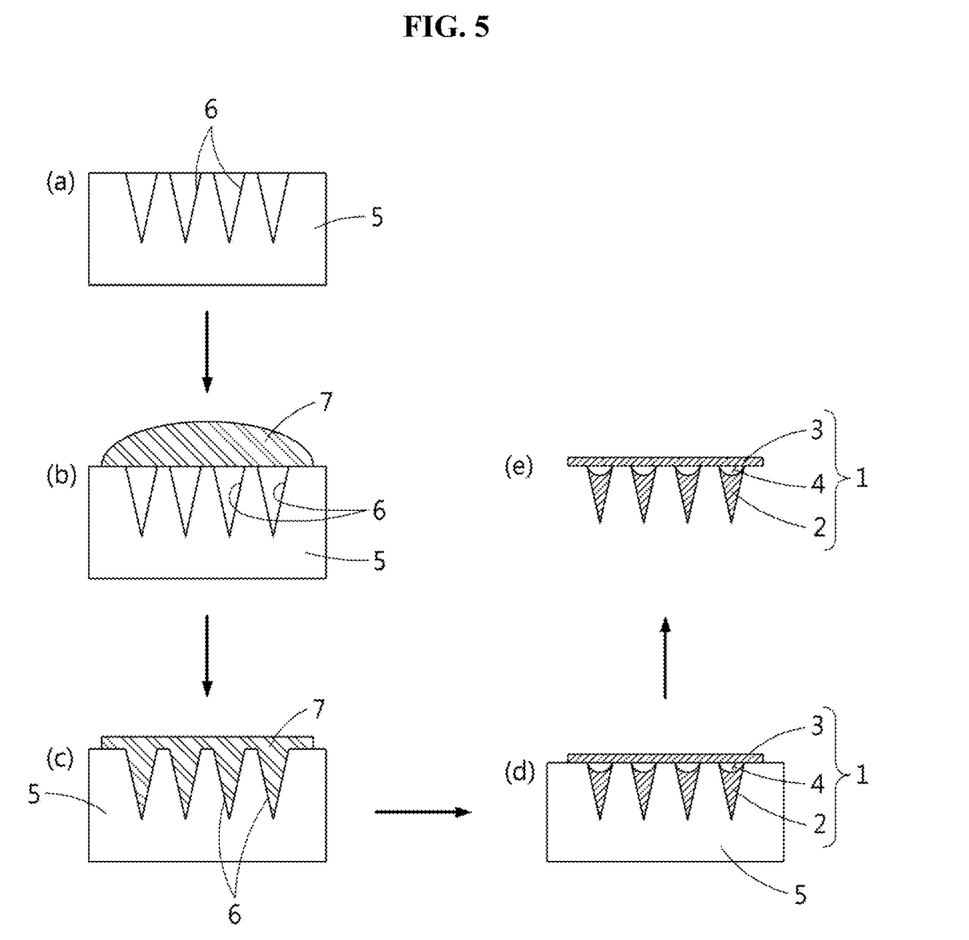
FIG. 5 is a view sequentially illustrating a cavity formation operation corresponding to a step of forming cavities illustrated in FIG. 4.

Referring to FIGS. 3 to 5, a method of manufacturing the micro-needle 1 according to an embodiment of the present disclosure includes step 10 of preparing a medicinal solution, step 20 of forming tips, and a step 30 of forming cavities.

In the step 10 of preparing a medicinal solution, a medicinal solution 7 (see FIG. 5) is prepared to form the micro-needle 1. Here, the medicinal solution 7 is formed of a water-soluble polymer including distilled water and hyaluronic acid. More particularly, the medicinal solution 7 is a 10% hyaluronic acid mixture prepared by mixing 1 g of hyaluronic acid with about 9 ml of distilled water.

More particularly, the medicinal solution 7 is prepared by mixing a biocompatible material with distilled water. Here, the biocompatible material includes any one or more selected from the group consisting of hyaluronic acid, alginic acid, pectin, carrageenan, chondroitin(sulfate), dextran (sulfate), chitosan, polylysine, collagen, gelatin, carboxymethyl chitin, fibrin, agarose, pullulan polylactide, polyglycolide (PGA), a polylactide-glycolide copolymer (PLGA), hyaluronic acid, alginic acid, carrageenan, chondroitin(sulfate), dextran(sulfate), chitosan, polylysine, collagen, gelatin, carboxymethyl chitin, fibrin, agarose, pullulan polyanhydride, polyorthoester, polyetherester, polycaprolactone, polyesteramide, poly(butyric acid), poly (valeric acid), polyurethane, polyacrylate, an ethylene-vinyl acetate polymer, acryl-substituted cellulose acetate, non-degradable polyurethane, polystyrene, polyvinyl chloride, polyvinyl fluoride, poly(vinylimidazole), chlorosulfonate polyolefin, polyethylene oxide, polyvinylpyrrolidone (PVP), polyethylene glycol (PEG), polymethacrylate, hydroxypropyl methylcellulose (HPMC), ethyl cellulose (EC), hydroxypropyl cellulose(HPC), carboxymethyl cellulose, cyclodextrin, and a copolymer of monomers and cellulose forming such a polymer.

In addition, the medicinal solution 7 is prepared by mixing the biocompatible material with an additive for improving mechanical strength. The additive is formed of one or more selected from the group consisting of trehalose, glucose, maltose, lactose, lactulose, fructose, turanose, melitose, melezitose, dextran, sorbitol, xylitol, palatinit, mannitol, poly((lactide), poly(glycolide), poly((lactide-co-glycolide), polyanhydride, polyorthoester, polyetherester, polycaprolactone, polyesteramide, poly(butyric acid), poly (valeric acid), polyurethane, polyacrylate, an ethylene-vinyl acetate polymer, acryl-substituted cellulose acetate, non-degradable polyurethane, polystyrene, polyvinyl chloride, polyvinyl fluoride, poly(vinylimidazole), chlorosulphonate polyolefin, polyethylene oxide, polyvinylpyrrolidone (PVP), polyethylene glycol (PEG), polymethacrylate, hydroxypropyl methylcellulose (HPMC), ethyl cellulose (EC), hydroxypropyl cellulose(HPC), carboxymethyl cellulose, and cyclodextrin and a copolymer of monomers forming such a polymer.

In addition, the medicinal solution 7 is prepared by mixing the biocompatible material with an effective ingredient. The effective ingredient may include a protein/peptide medicine, but the present disclosure is not limited thereto. The effective ingredient may include a hormone, a hormone analogue, an enzyme, an enzyme inhibitor, a signal transduction protein or a portion thereof, an antibody or a portion thereof, a single-chain antibody, a binding protein or a binding domain thereof, an antigen, an adherent protein, a structural protein, a regulatory protein, a toxin protein, a cytokine, a transcription regulator, a blood coagulation factor, a vaccine, etc. More particularly, the protein/peptide medicine includes insulin, insulin-like growth factor 1 (IGF-1), growth hormone, erythropoietin, granulocyte-colony stimulating factors (G-CSFs), granulocyte/macrophage-colony stimulating factors (GM-CSFs), interferon alpha, interferon beta, interferon gamma, interleukin-1 alpha and beta, interleukin-3, interleukin-4, interleukin-6, interleukin-2, epidermal growth factors (EGFs), calcitonin, adrenocorticotropic hormone (ACTH), tumor necrosis factor (TNF), atobisban, buserelin, cetrorelix, deslorelin, desmopressin, dynorphin A (1-13), elcatonin, eleidosin, eptifibatide, growth hormone releasing hormone-II (GHRH-II), gonadorelin, goserelin, histrelin, leuprorelin, lypressin, octreotide, oxytocin, pitressin, secretin, sincalide, terlipressin, thymopentin, thymosine, triptorelin, bivalirudin, carbetocin, cyclosporine, exedine, lanreotide), luteinizing hormone-releasing hormone (LHRH), nafarelin, parathyroid hormone, pramlintide, enfuvirtide (T-20), thymalfasin, ziconotide, etc.

In addition, the medicinal solution 7 is a mixed solution including a solvent that may dissolve the biocompatible material. Here, examples of the solvent include an inorganic or organic solvent including distilled water (DI water), methanol, ethanol, chloroform dibutyl phthalate, dimethyl phthalate, ethyl lactate, glycerin, isopropyl alcohol, lactic acid, propylene glycol, or the like.

In step 20 of forming tips, the tips 2 are formed using the medicinal solution 7. An empty space, i.e., the cavity 4, is formed in each of the formed tips 2 (step 30). The step 30 of forming the cavities 4 is described in detail with reference to FIGS. 4 and 5.

Step 30 of forming the cavities includes step 31 of filling grooves 6 of a mold 5, which correspond to a desired shape of the tips 2 of the micro-needle 1, with the medicinal solution 7, step 32 of centrifuging the medicinal solution 7 filled in the grooves 6, and step 33 of drying the medicinal solution 7 and then removing the same from the mold 5, as illustrated in FIGS. 4 and 5.

In step 31 of filling the grooves 6 of the mold 5 with the medicinal solution 7, the mold 5 including the grooves 6 is prepared as illustrated FIG. 5(*a*), and then the medicinal solution 7 is applied to the grooves 6 as illustrated in FIG. 5(*b*). Here, the amount of the medicinal solution 7 is exemplified as about 0.14 g. The applied medicinal solution 7 is distributed to the grooves 6 and is filled with the medicinal solution 7, as illustrated in FIG. 5(*c*).

The medicinal solution 7 filled in the grooves 6 is centrifuged and, by centrifugal force, the cavities 4 are formed as illustrated in FIG. 5(*d*). In this embodiment, the centrifugation is exemplified as performing at about 3000 rpm and 25° C. for about 20 minutes. In this case, the cavities 4 are formed in an upper part of the grooves 6 filled with the medicinal solution 7, thereby being formed between the grooves 6 and the base 3 formed to cover the grooves 6.

When the cavities 4 are formed in the grooves 6 filled with the medicinal solution 7 by centrifugation as described above, the medicinal solution 7 is dried as illustrated in FIG. 5(*e*) and the mold 5 is removed from the dried medicinal solution 7 (step 33). Here, the medicinal solution 7 is naturally dried at room temperature. Since the cavities 4 are provided inside the tips 2, the cavities 4 are not observed even under an electron microscope.

For reference, a formation condition of the cavities 4 may be varied depending upon an evaporation rate of the medicinal solution 7, particularly a solvent in the mixed solution including hyaluronic acid; the concentration of the medicinal solution 7; and the amount of the medicinal solution 7 filled in the grooves 6 of the mold 5. Accordingly, the volumes of the cavities 4 may be changed by changing a condition of the medicinal solution 7 forming the micro-needle 1, whereby the micro-needle 1 may be applied to various medication conditions.

Figure 6:
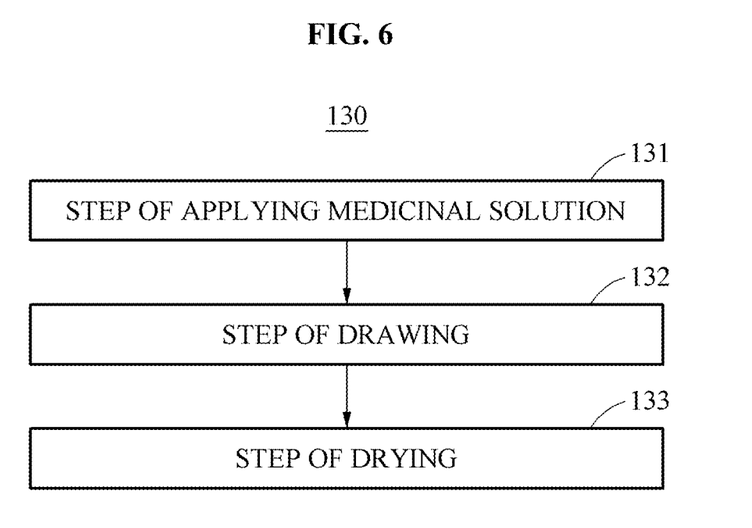
FIG. 6 is a flowchart schematically showing sub-steps of a step of forming cavities according to another embodiment.

In addition, FIG. 6 illustrates another embodiment of forming cavities 4. As illustrated in FIG. 6, step 130 of forming cavity 4 according to another embodiment includes step 131 of applying a medicinal solution 7, step 132 of drawing the medicinal solution 7, and step 133 of drying the medicinal solution 7.

Figure 7:
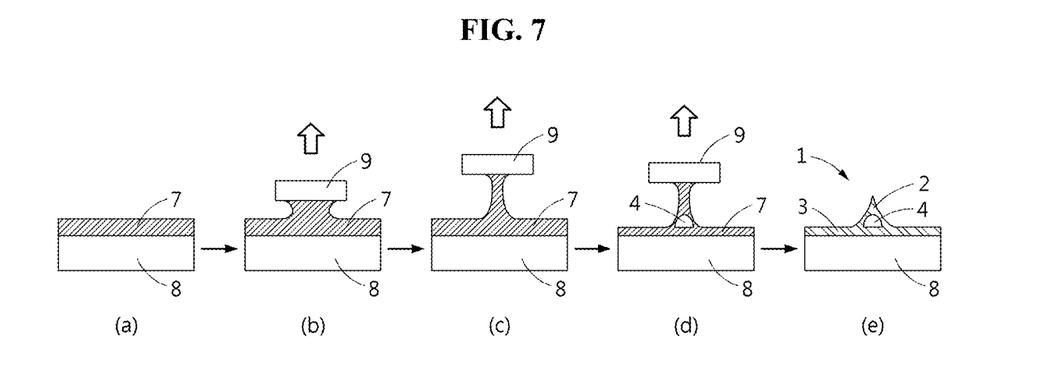
FIG. 7 is a view sequentially illustrating a cavity formation operation corresponding to a step of forming cavities according to another embodiment illustrated in FIG. 6.

In step 131 of applying the medicinal solution 7, the medicinal solution 7 is applied onto a supporter 8 as illustrated in FIG. 7(*a*). Here, the medicinal solution 7 is exemplified as an 8% hyaluronic acid solution prepared by mixing 0.8 g of hyaluronic acid with 9.2 ml of distilled water. In addition, the supporter 8 includes a substrate and about 10 μl of the medicinal solution 7 is applied to the supporter 8.

Subsequently, as illustrated in FIGS. 7 (*b*) to (*d*), the medicinal solution 7 is drawn vertically from the support 8 until the cavity 4 is formed (step 132). Here, the drawing operation is exemplified as vertically lifting the medicinal solution 7 by means of a drawing member 9, such as tweezers. Through such a drawing step 132, the cavity 4 is formed due to the viscosity of the medicinal solution 7. The medicinal solution 7, in which the cavity 4 has been formed, is blow-dried at 50° C. and a flow rate of 300 L/min for about 10 to 15 seconds (step 133). As a result, a micro-needle 1 is finally manufactured as illustrated in FIG. 7(*e*).

The micro-needle 1 having the aforementioned configuration was injected into the skin S. Injection degrees thereof are compared in FIG. 8.

Figure 8:
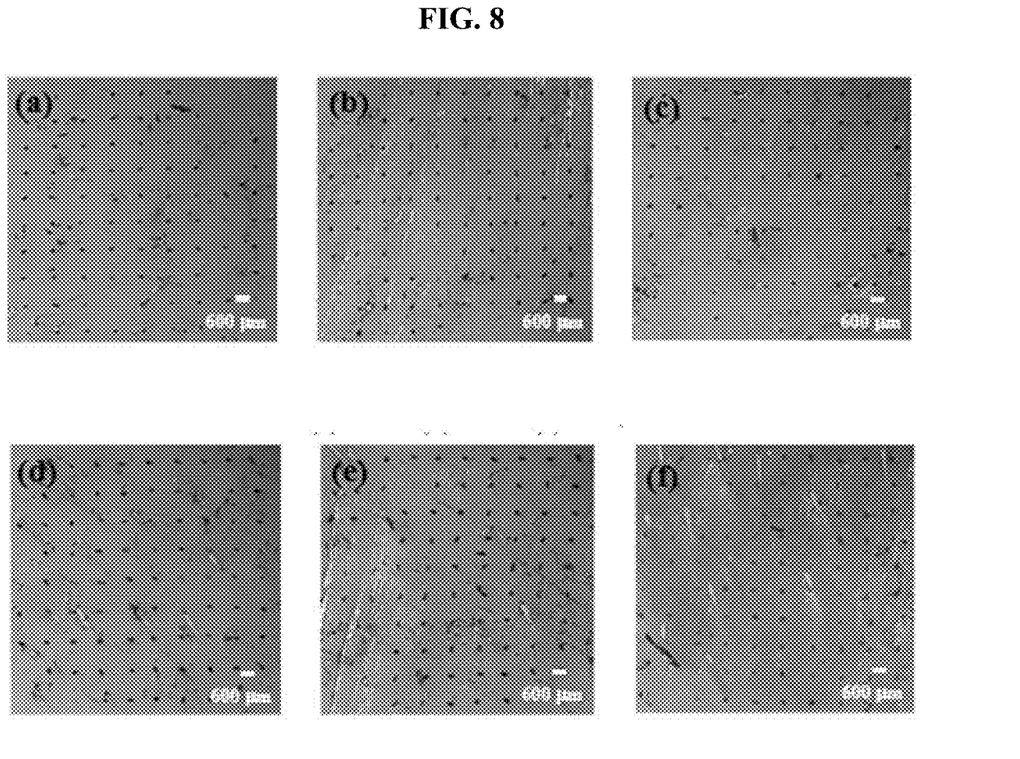
FIG. 8 illustrates images to compare penetration degrees of a micro-needle according to the present disclosure and a conventional micro-needle injected into the skin.

FIGS. 8(*a*), (*b*) and (*c*) illustrate states in which the micro-needle 1 including the cavities 4 according to the present disclosure was applied to the skin S with a force of each of 10 N, 20 N and 30 N for 10 seconds. In addition, FIGS. 8(*d*), (*e*), and (*f*) illustrate states in which a conventional micro-needle (not shown) not including cavities was applied to the skin S with a force of each of 10 N, 20 N, and 30 N for 10 seconds. Here, the skin S was prepared by thawing porcine skin, which had been stored at −20° C., at 32° C. for one and a half hours to two hours and then fixing the porcine skin to a fixing plate for 15 minutes, and was subjected to the experiment.

Referring to FIG. 8, when the micro-needle 1 according to the present disclosure and the conventional micro-needle (not shown) were respectively injected by applying a force of 10 N, about 80% of a medicine was administered to the skin S. In addition, when a force of 30 N was applied, almost all of the medicine was administered to the skin S. Accordingly, it can be confirmed that, although the cavities 4 are present in the micro-needle 1 as in the present disclosure, mechanical force required to penetrate the skin S is not greatly affected.

Figure 9:
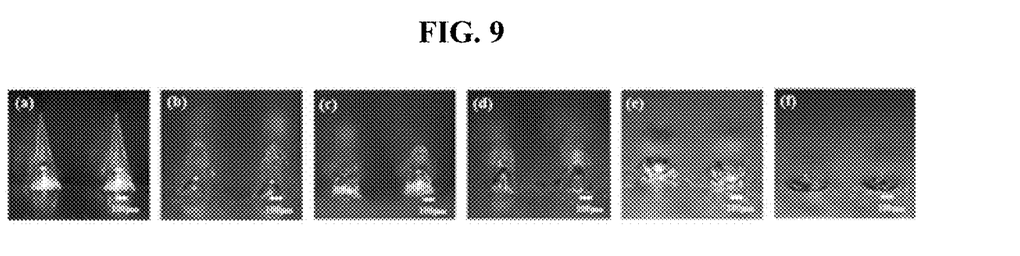
FIG. 9 illustrates optical microscope images showing melting degrees over time of a micro-needle according to the present disclosure injected into the skin.
Figure 10:
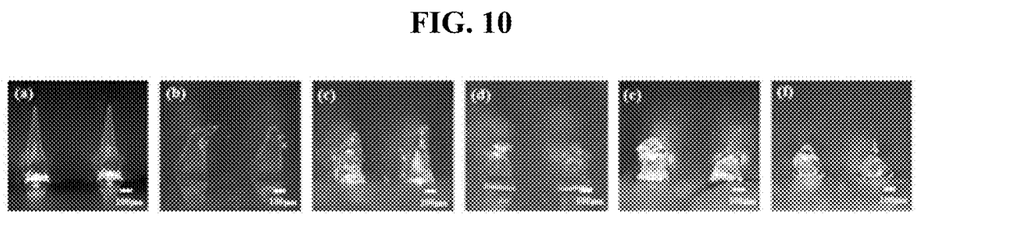
FIG. 10 illustrates optical microscope images showing melting degrees over time of a conventional micro-needle injected into the skin.

Referring to FIGS. 9 and 10, a melting degree of the micro-needle 1 administered to the skin S is compared to a conventional case. FIGS. 9(*a*) to (*f*) illustrate optical microscope images showing a melting degree of the micro-needle 1 including the cavities 4 according to the present disclosure, FIGS. 10(*a*) to (*f*) illustrate optical microscope images showing a melting degree of the conventional micro-needle (not shown). Here, FIGS. 9 and 10 illustrate optical microscope images representing a melting state of a medicine at time points of 1 minute, 5 minutes, 10 minutes, 15 minutes, 30 minutes, and 60 minutes, respectively.

As illustrated in FIGS. 9 and 10, while the micro-needle 1 according to the present disclosure is completely melted, the conventional micro-needle 1 is not melted and remains. That is, a melting speed of the tips 2 of the present disclosure increases by rapidly melting up to the points of the tips 2 where the cavities 4 are present. Here, when upper parts of the tips 2 of the present disclosure, where the cavities 4 are present, are completely melted, remaining parts of the tips 2 are crushed toward the base 3 without being separated from the base 3.

Figure 11:
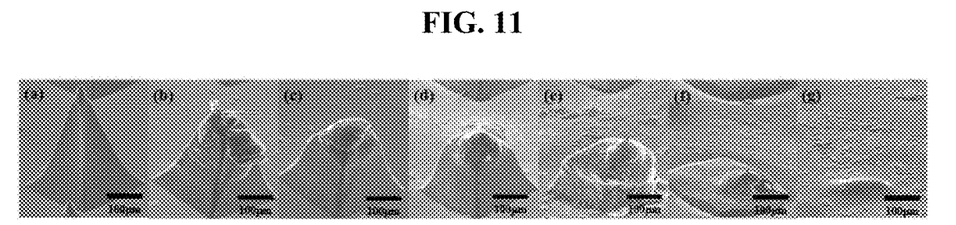
FIG. 11 illustrates electron microscope images showing a melting degree over time of a micro-needle according to the present disclosure injected into the skin.
Figure 12:
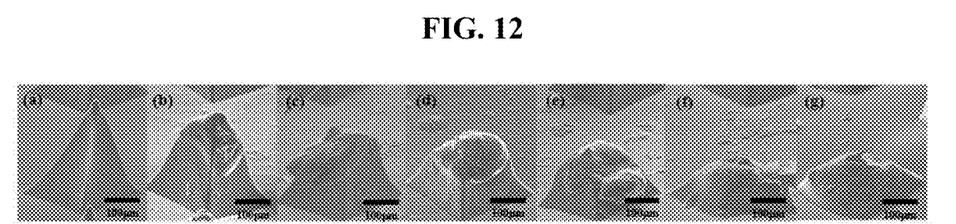
FIG. 12 illustrates electron microscope images showing a melting degree over time of a conventional micro-needle injected into the skin.

FIG. 11 illustrates electron microscope images showing a melting degree over time of the micro-needle 1 according to the present disclosure, and FIG. 12 illustrates electron microscope images showing a melting degree over time of a conventional micro-needle (not shown). FIGS. 11(*a*) to (*f*) and FIGS. 12(*a*) to (*f*) illustrate a melting state of the medicine at time points of 1 minute, 5 minutes, 10 minutes, 15 minutes, 30 minutes, and 60 minutes, respectively.

Referring to FIGS. 11 and 12, it can be confirmed that melting degrees are similar to a time point of 5 minutes regardless of the presence of the cavity 4, but, after the site at which the cavity 4 is present, has been melted, a melting speed of the micro-needle 1 according to the present disclosure is high. That is, while the tip 2 of the micro-needle 1 according to the present disclosure is completely melted, the tip of the conventional micro-needle is not completely melted.

Figure 13:
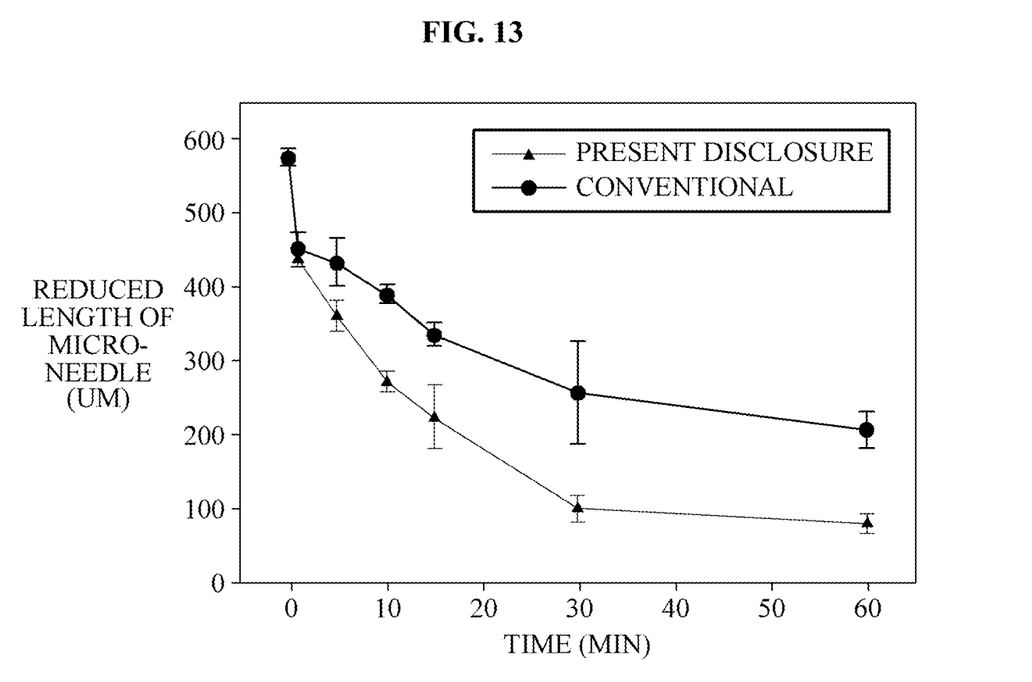
FIG. 13 is a graph showing tip length reduction by melting over time of a micro-needle of the present disclosure and a conventional micro-needle.
Figure 14:
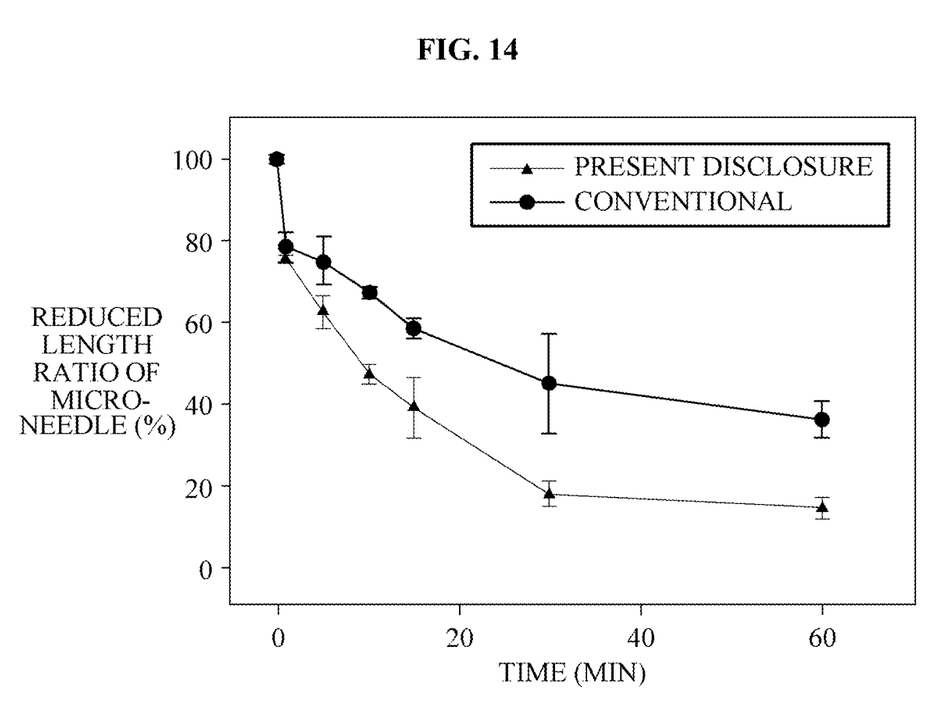
FIG. 14 is a graph showing tip length reduction rates by melting over time of a micro-needle of the present disclosure and a conventional micro-needle.

FIGS. 13 and 14 illustrate graphs comparing melting degrees of the micro-needle 1 according to the present disclosure and the conventional micro-needle. As illustrated in FIGS. 13 and 14, it can be confirmed that, in the case of the micro-needle 1 according to the present disclosure, a melting time of the tips 2, which have been injected into the skin S, is shorter, compared to the conventional case. Here, the depth of the medicine of the tips 2 administered to the skin S is about ½ to ⅔ of the total length of the tips 2. Accordingly, referring to FIGS. 13 and 14, it can be confirmed that, in delivering a fixed amount of medicine, the micro-needle 1 of the present disclosure is more advantageous, compared to the conventional case.

Meanwhile, the sizes of the cavities 4 formed in the aforementioned tips 2 may be controlled by adjusting the amount, evaporation rate, and evaporation temperature of the medicinal solution 7, the shapes of the grooves 6 of the mold 5 for manufacturing the micro-needle 1, the viscosity of the medicinal solution 7, the concentration of the medicinal solution 7, a used solvent type, and the thickness of the medicinal solution 7 covering the grooves 6.

Figure 15A:
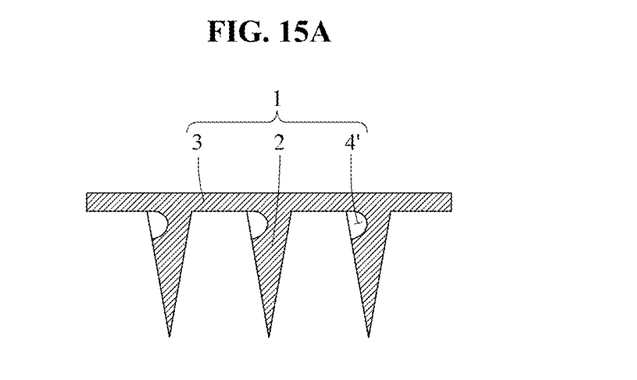
FIGS. 15A, 15B, 15C illustrate schematic sectional views of various modifications of a micro-needle according to the present disclosure.
Figure 15B:
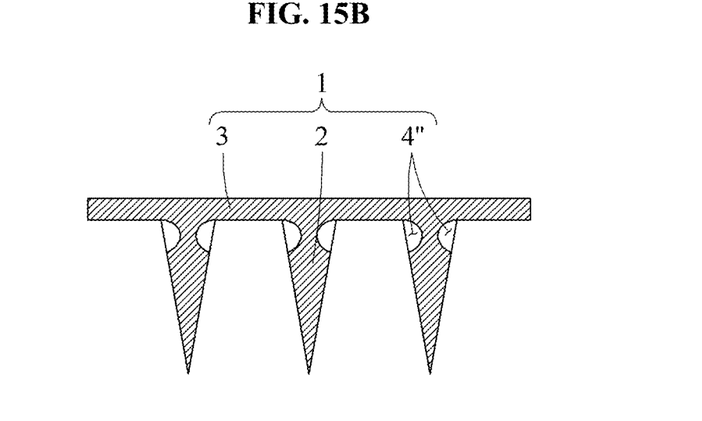
Figure 15C:
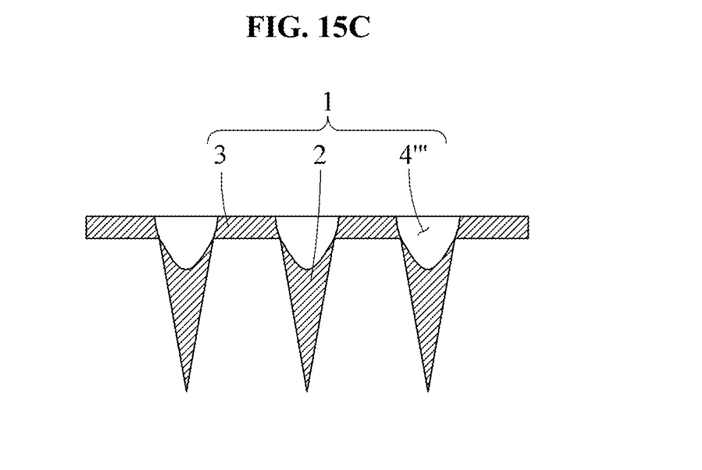

In addition, although the cavities 4 are illustrated and exemplified as being formed inside the tips 2 in the aforementioned embodiments, the present disclosure is not limited thereto. That is, one cavity 4' may be formed outside each of the tips 2, as illustrated in FIG. 15A, or at least two cavities 4" may be formed outside each of the tips 2 as illustrated in FIG. 15B. Further, as illustrated in FIG. 15C, a cavity 4''' may be formed between each of the tips 2 and the base 3. In addition, although not illustrated in detail, a cavity 4 may be formed to extend in a circumferential direction along an outer circumferential surface of each of the tips 2.

Hereinafter, a modification of the method of manufacturing the micro-needle 1 is described referring to FIGS. 16 and 17.

Figure 16:
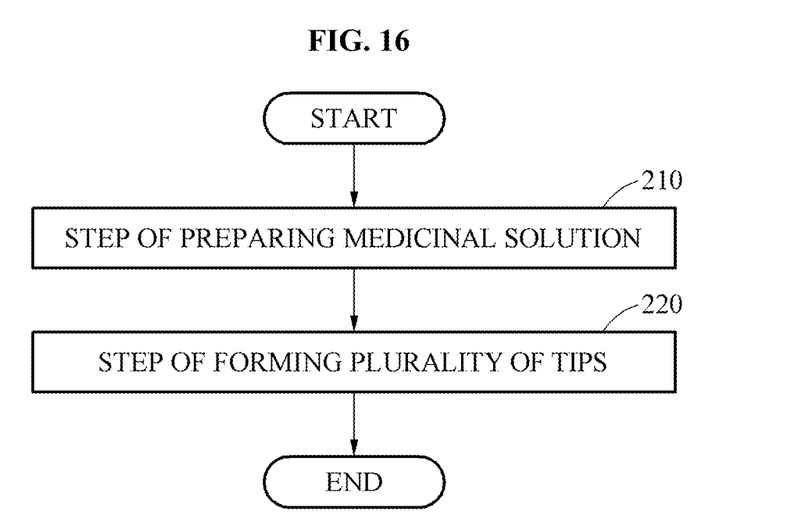
FIG. 16 is a flowchart schematically showing another embodiment of a method of manufacturing a micro-needle according to the present disclosure.
Figure 17:
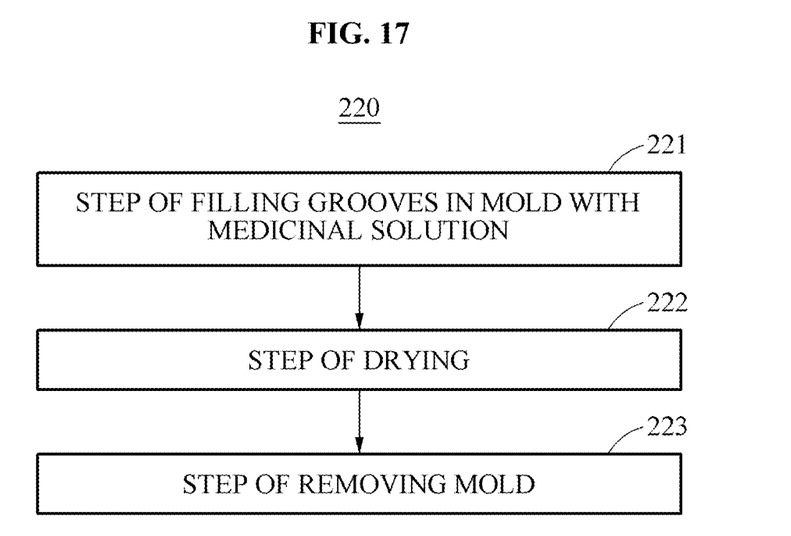
FIG. 17 is a flowchart schematically showing sub-steps of a step of forming a plurality of tips shown in FIG. 16.

Referring to FIGS. 16 and 17, a method of manufacturing the micro-needle 1 according to an embodiment of the present disclosure includes a step of preparing a medicinal solution 210 and step 220 of forming a plurality of tips 2. Accordingly, the micro-needle 1 is manufactured in a one-step manner.

In the step of preparing a medicinal solution 210, the medicinal solution 7 for forming the micro-needle 1 is prepared (see FIG. 6). This medicinal solution 7 is a solution prepared by mixing a solvent with a biocompatible material as described above. The medicinal solution 7 is exemplified as a 1% water-soluble polymer solution prepared by dissolving a biocompatible material including 0.01 g of hyaluronic acid in a solvent including 1 ml of distilled water (DW).

In step 220 of forming the plurality of tips 2, the tips 2, in each of which at least one cavity 4 is formed, are formed using the medicinal solution 7. Step 220 of forming the tips 2 is described in detail with reference to FIGS. 17 and 18.

Figure 18:
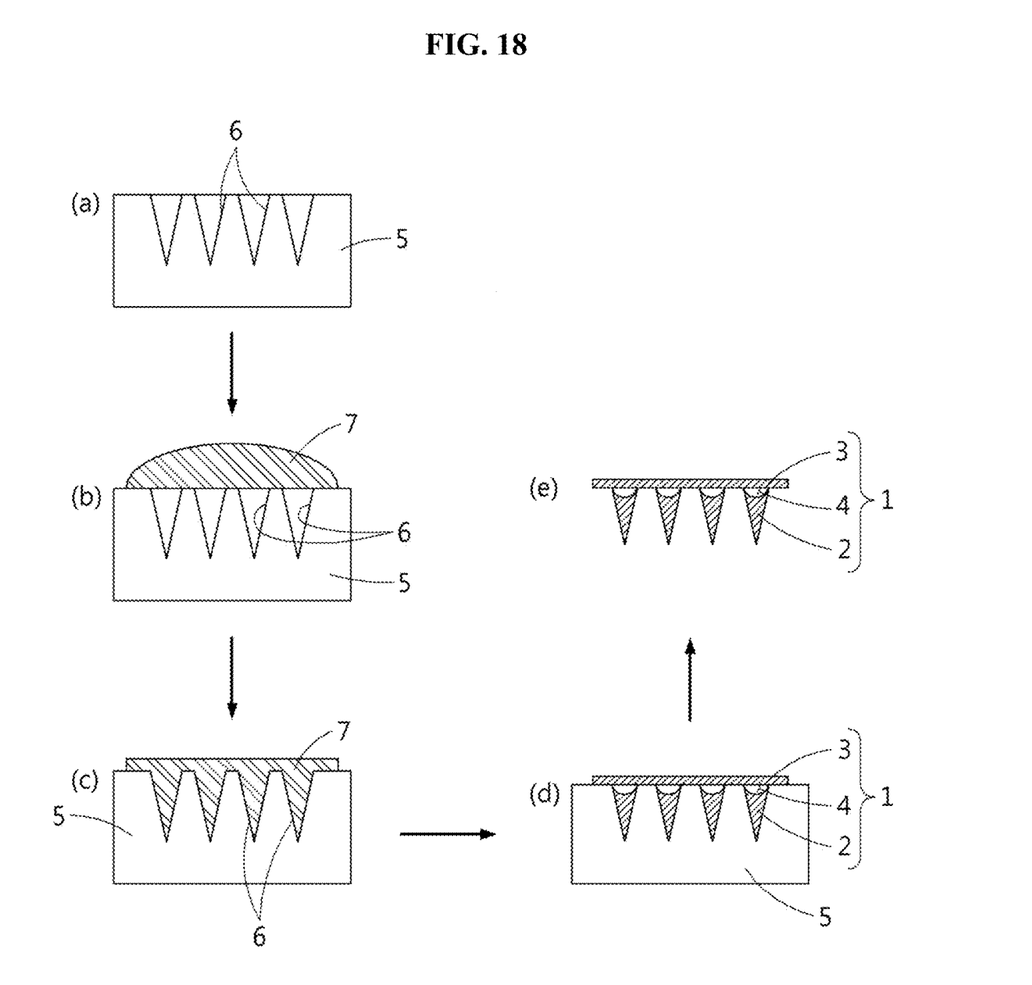
FIG. 18 sequentially illustrates a cavity formation operation corresponding to the method of manufacturing a micro-needle shown in FIG. 16.

Step 220 of forming the tips 2 includes step 221 of filling at least one groove 6 in a mold 5 with the medicinal solution 7, step 222 of drying the medicinal solution 7 filled in the groove 6, and step 223 of removing a formed micro-needle 1 from the mold 5, as illustrated in FIGS. 17 and 18.

The mold 5 includes a plurality of grooves 6 corresponding to the shapes of the tips 2 of the micro-needle 1 as illustrated in FIG. 18(a). The medicinal solution 7 is supplied to the mold 5 as illustrated in FIG. 18(b) and then is distributed to and fills the grooves 6 as illustrated in FIG. 18(c) (step 221).

Subsequently, the medicinal solution 7 filled in the grooves 6 is dried to form at least one cavity 4 as illustrated in FIG. 18(d) (step 222). In step 222 of drying the medicinal solution 7, the medicinal solution 7 filled in the grooves 6 is dried by evaporating moisture therein using at least one of natural drying, vacuum drying and drying under pressure. Here, examples of the drying under pressure include drying using an external force such as temperature, pressure, or blown air.

In step 222 of drying the medicinal solution 7, the medicinal solution 7 is dried by evaporation of moisture, and thus, the cavities 4 are formed. For reference, in this embodiment, step 222 of drying the medicinal solution 7 is exemplified by repeating a step of applying vacuum for 10 seconds at 0.08 MPA and then releasing the vacuum for 10 seconds by purge eight times. Subsequently, 0.3 g of the medicinal solution 7, as a 1% hyaluronic acid mixture, is further supplied to the mold 5, and then the medicinal solution 7 filled in the grooves 6 is dried by applying a vacuum of 600 mmHg for 10 minutes. Finally, step 222 of drying the medicinal solution 7 is exemplified by drying the medicinal solution 7 at 70° C. for about 40 minutes.

Meanwhile, step 222 of drying the medicinal solution 7 may be modified by a method of cooling the medicinal solution 7 filled in the grooves 6 under a reduced pressure or a normal pressure to solidify the medicinal solution 7 such that at least one cavity 4 is formed. In the case of the method of solidifying the medicinal solution 7, evaporation of moisture in the medicinal solution 7 is induced by cooling under a reduced pressure or a normal pressure, thereby forming the cavities 4.

The sizes of the cavities 4 formed through step 222 of drying the medicinal solution 7 may be controlled by adjusting the amount, evaporation rate, or evaporation temperature of the medicinal solution 7, the shapes of the grooves 6 of the mold 5 for manufacturing the micro-needle 1 (see FIG. 18), the viscosity of the medicinal solution 7, the concentration of the medicinal solution 7, a used solvent type, or the thickness of the medicinal solution 7 covering the grooves 6.

After the cavities 4 are formed through step 222 of drying the medicinal solution 7, the mold 5 is removed from the dried medicinal solution 7 as illustrated in FIG. 18(e). Finally, the micro-needle 1 is manufactured.

Figure 19:
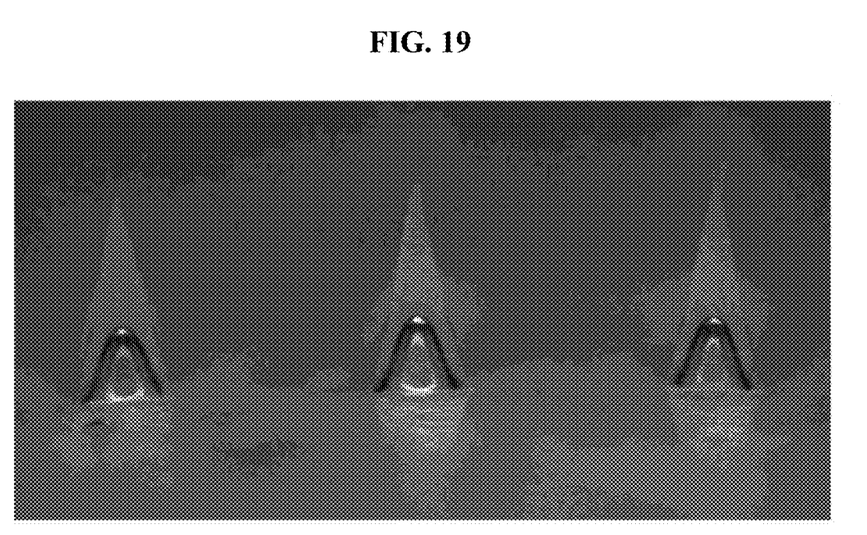
FIG. 19 illustrates an optical microscope image of a micro-needle manufactured according to the present disclosure.

Optical microscope images of the micro-needle 1 manufactured according to the aforementioned method are illustrated in FIG. 19. Referring to FIG. 19, it can be confirmed that an empty space, i.e., the cavity 4, is formed inside each of the tips 2 of the micro-needle 1.

In accordance with the present disclosure having the aforementioned configuration, first, a melting speed of a tip, in which a cavity is formed, may be increased, whereby it is possible to administer a fixed amount of medicine in a short time.

Second, the volume of the cavity may be controlled by adjusting a condition of forming the cavity, whereby application thereof to various medicines may be accomplished.

Third, since the cavity is formed by centrifugation or drawing, a manufacturing method is simple and thus mass-production is possible.

Fourth, a fixed amount of medicine may be locally supplied, which contributes to improvement in therapeutic effect.

Fifth, a fixed amount of medicine may be supplied, which contributes to increase in the reliability of the patient.

Sixth, the size of the cavity may be controlled by adjusting the amount, evaporation rate, or evaporation temperature of the medicinal solution, internal shapes of grooves of a mold for manufacturing the micro-needle, the viscosity of a medicinal solution, the concentration of a medicinal solution, a used solvent type, or the thickness of a medicinal solution covering the grooves, whereby the micro-needle according to the present disclosure may be applied to various medications and administration conditions.

Seventh, since the micro-needle according to the present disclosure is manufactured in a one-step manner wherein the medicinal solution is supplied to the mold and then dried, a manufacturing method thereof is simple and it is easy to mass-produce the same.

Eighth, since the cavity is formed in at least one portion of the interior, an outer side, a middle part, or the like of a needle, diverse forms are advantageously possible.

While the present disclosure has been described referring to the preferred embodiments, those skilled in the art will appreciate that many modifications and changes can be made to the present disclosure without departing from the spirit and essential characteristics of the present disclosure.

DESCRIPTION OF SYMBOLS

1: MICRO-NEEDLE
2: TIP
3: BASE
4: CAVITY

What is claimed is:

1. A micro-needle, comprising:
a plurality of tips formed of a medicine that penetrate into and are melted in skin, wherein each of the plurality of tips includes a bottom side and an end portion and extends from the bottom side to the end portion in a first direction; and
a base supporting the tips and having an upper side extending in a second direction vertical to the first direction,
wherein a cavity is formed between the base and each of the tips so that the tips do not remain on the base although the base is detached from the skin,
wherein the base and the tips are integrally formed with each other, and
wherein the cavity is formed between the upper side of the base and the bottom side of each of the tips, wherein the upper side of the base is combined to the bottom side of each of the tips only along an edge of the bottom side of each of the tips,
wherein the cavity includes a bottom end and an upper end,
wherein a size of a cross section of the cavity decreases along the first direction from the bottom end of the cavity to the upper end of the cavity, and
wherein the cross section of the cavity is parallel to the second direction and is vertical to the first direction.

2. The micro-needle according to claim 1, wherein the cavity is formed inside of each of the tips.

3. A micro-needle comprising:
a plurality of tips formed of a medicine that penetrate into and are melted in skin, wherein each of the plurality of tips is in a cone shape and includes a bottom side, an end portion and an outer surface and extends from the bottom side to the end portion in a first direction; and
a base supporting the plurality of tips and having an upper side extending in a second direction vertical to the first direction,
wherein a size of a cross section of each of the tips decreases along the first direction from the bottom side to the end portion,
wherein at least one cavity is formed in each of the tips, and
wherein each of the at least one cavity is a recess formed inwardly from the outer surface of each of the tips,
wherein the at least one cavity includes a first cavity and a second cavity formed in each of the tips, and
wherein the first cavity is a first recess formed inwardly from the outer surface and the second cavity is a second recess formed inwardly from the outer surface, the first recess and the second recess being formed inwardly from opposite sides of the outer surface.

* * * * *